United States Patent [19]

Grieshaber

[11] Patent Number: 4,813,401
[45] Date of Patent: Mar. 21, 1989

[54] RETRACTOR

[75] Inventor: Herman R. Grieshaber, Glenview, Ill.

[73] Assignee: Grieshaber Manufacturing Company, Norridge, Ill.

[21] Appl. No.: 935,480

[22] Filed: Nov. 26, 1986

[51] Int. Cl.[4] .............................................. A61B 17/02
[52] U.S. Cl. ........................................ 128/20; 128/17
[58] Field of Search .................................. 128/17–20; 248/223.1, 223.2, 230; 269/322–328

[56] References Cited

U.S. PATENT DOCUMENTS

| | | | |
|---|---|---|---|
| 2,693,795 | 11/1954 | Grieshaber | 128/20 |
| 3,384,077 | 5/1968 | Gauthier | 128/20 |
| 3,509,873 | 5/1970 | Karlin et al. | 128/17 |
| 3,710,783 | 1/1973 | Jascalevich | 128/20 |
| 3,749,088 | 7/1973 | Gauthier | 128/20 |
| 4,010,741 | 3/1977 | Gauthier | 128/20 |
| 4,254,763 | 3/1981 | McCready et al. | 128/20 |
| 4,355,631 | 10/1982 | LeVahn | 128/20 |
| 4,461,284 | 7/1984 | Fackler | 128/20 |
| 4,467,791 | 8/1984 | Cabrera et al. | 128/20 |
| 4,617,916 | 10/1986 | LeVahn et al. | 128/20 |

Primary Examiner—Benoit Castel
Assistant Examiner—T. J. Wallen
Attorney, Agent, or Firm—Neuman, Williams, Anderson & Olson

[57] ABSTRACT

A surgical retractor for adjustable mounting on a supported holder includes an elongated stem of cylindrical cross-sectional configuration and blade means attached to one end of the stem, the stem being optionally provided with a plurality of spaced circumferential first means for selective engagement by adjustable complemental second means for restraining longitudinal movement of the stem in one direction, and optionally including an inner section hingedly connected to an outer section, providing a handle for pulling or rotating the retractor.

A holder for a surgical retractor and frame support for the holder assume a nonrotating relation where the frame support has a section of substantially cylindrical cross-sectional configuration and has a longitudinally extending indentation, a portion of the frame support is encompassed by a section of the holder, and the holder section has protruding means for engaging the indentation of the frame support section.

11 Claims, 2 Drawing Sheets

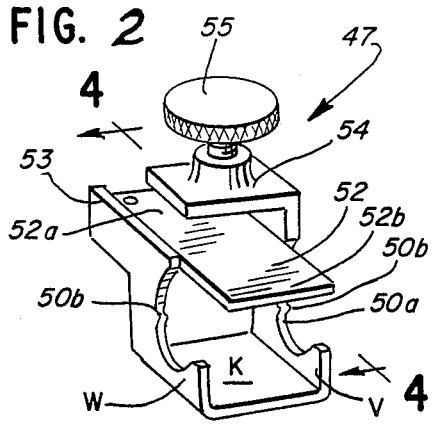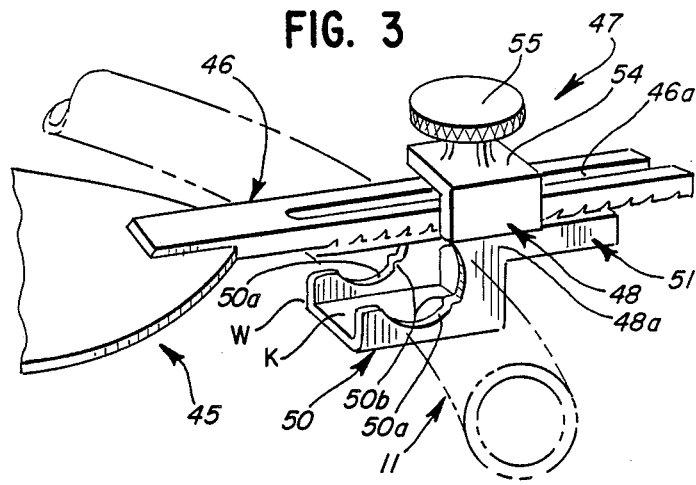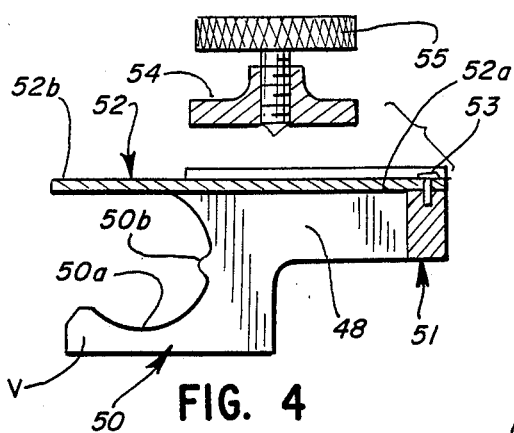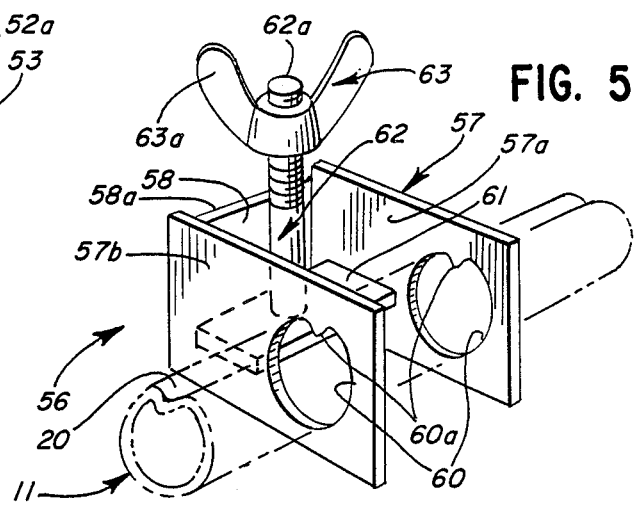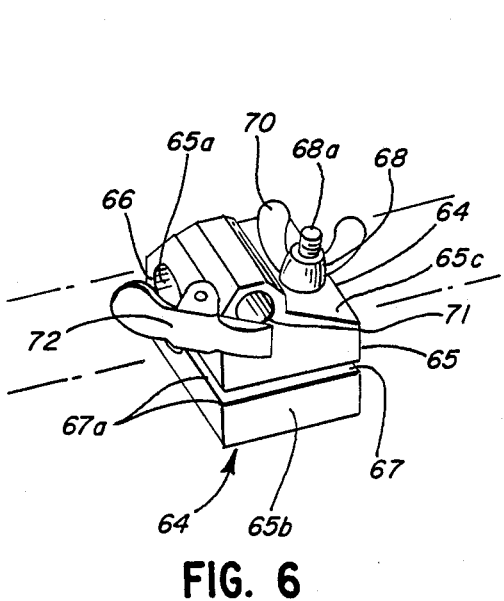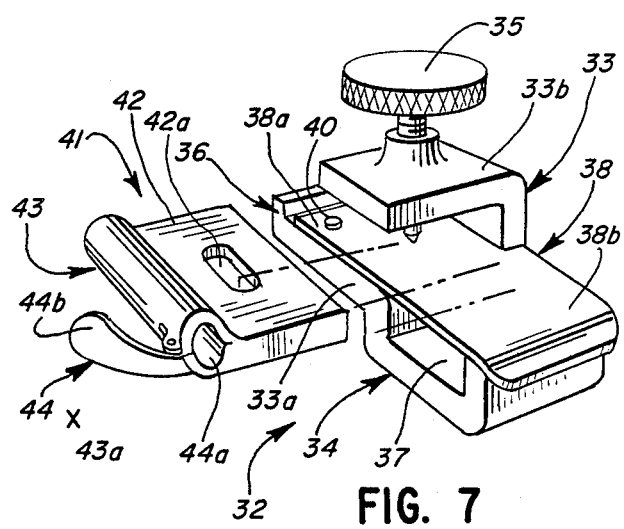

RETRACTOR

BACKGROUND OF THE INVENTION

A. Field Of The Invention

This invention relates to surgical implements, and, in particular, to devices known as retractors.

B. Brief Description Of The Prior Art

Retractors are devices used by the surgeon to hold open a large incision while a major operation is performed. They are supported above the site of the incision by a retractor frame which is secured to the operating table, usually in a horizontal position. Such frames are available in a variety of sizes and configurations in order to suit the particular surgical procedure to be performed. For example, such frames may be linear, circular or U-shaped, and they may be constructed of flat steel strips or of tubular steel.

Retractors are mounted upon the retractor frame by holders which both secure the retractor to the frame and provide a means by which the degree of retraction may be adjusted. Typically, the retractor itself is made of surgical stainless steel and comprises a smooth blade which engages the incision, a stem by which the retractor is supported, and a handle by which the surgeon pulls the retractor to the desired position. A fastener on the holder grasps the stem of the retractor and maintains it in the desired position.

As can be clearly seen in FIG. 1 of the drawings, in any given surgical procedure, a variety of retractors may be utilized. One problem which has arisen under such circumstances is that the handle, or proximal, ends of conventional solid-stemmed retractors extend out from the operating field and may become obstacles to the surgeon's freedom of movement. Thus, the surgeon's attention must not only be directed to the procedure at hand, but must also be directed to avoiding contact with the ends of the various retractors which may be in use.

Another attribute of conventional retractors is that their stems are generally flat in cross-section, and no adjustment of the planar orientation of the blade is therefore possible. This can be a significant drawback to obtaining an optimal exposure of the operative site.

Conventional retractors are, as shown by FIG. 1, secured to their holders by a variety of fasteners. Such fasteners permit the position of the retractor to be changed by first loosening a wing nut or other screw type member, adjusting the retractor to the desired position, and then retightening the nut or screw to lock the retractor into its new position. This procedure is somewhat time consuming, and it not only lengthens the time required to first open the incision to the desired degree, but, more importantly, makes adjustment during the operation considerably more cumbersome than necessary at a time when speed is most desirable.

As with conventional retractors, certain inconveniences are associated with the use of conventional retractor holders.

Where a retractor frame of circular cross section is employed, the holder typically is a solid block of metal having a narrow cut extending from one edge into a central cylindrical passage through which the retractor frame may be inserted, and having a fastener which, when tightened, compresses the block, clamp-like, onto the frame. Such holders must be attached to the frame by sliding each one, in its proper sequence, onto the end of the frame. If one type of holder is put onto the frame out of proper sequence, or if the sequence of holders is later desired to be changed, all holders between the one desired to be moved and the nearest frame end must be removed and then replaced. In such circumstances, the frame supports themselves must be released and then resecured in order to accomplish the desired change.

A further drawback inhering in the conventional holder designed for use on a cylindrical cross-section frame is that rotation of the holder about the frame may occur. While generally sufficient clamping action is obtained when the conventional aluminum holder is clamped to a conventional tubular stainless steel frame, the union of these two smooth surfaces—the interior surface of the holder and the exterior surface of the frame—nonetheless can permit some rotation if, for example, the stem of the retractor carried by the holder is accidentally struck from above.

A further drawback of conventional holders lies in their solid construction, particularly the cylindrical passage through which the retractor frame is passed. The difficulty with this construction lies in the fact that such a holder cannot slide around any curved portions of a frame, such as a U-shaped frame, thus limiting the range of positions into which the holder can be placed.

SUMMARY OF THE INVENTION

Thus, it is an object of the present invention to overcome the inconvenience and disadvantages of the conventional retractor components in a number of respects.

In particular, it is one object of the invention to provide a retractor having stem which does not present a physical obstacle to the surgeon's movements during the operation.

A second object of the present invention is to provide a retractor which is angularly adjustable so as to maximize the range of blade positions available to the surgeon.

An additional object is to provide a retractor which permits the degree of retraction to be adjusted simply and quickly.

A further object of the present invention is to provide a retractor holder which is easily moveable to a new position on the retractor frame without the necessity of disturbing other retractor structures.

A still further object is to provide a means of preventing rotation of a retractor holder with respect to the supporting frame.

Yet another object is to provide a retractor holder for use with retractor frames of round cross-section which is moveable along curved sections of that frame.

In accordance with the foregoing objects, the present invention includes a number of improvements over conventional retractor devices.

One feature of the present invention is a retractor stem having a round cross-section. The advantage of a round stem over a flat or other shaped stem is that it may be rotated within the holder, thus permitting planar adjustment of the retractor blade and increasing the range of retractor positions available to the surgeon. Not only is this advantageous insofar as the optimal engagement of the blade with the incision is concerned, but it provides the further benefit of enabling the blade to be rotated away from the patient prior to its removal from the site of the operation.

Another aspect of the invention is a retractor having an elongated stem with a hinge disposed between the proximal handle end and the distal blade end. The hinge permits a section of the stem of the retractor to fold down out of the surgeon's way after the retractor blade has been drawn into the desired position. One advantage of this folding capability is that the surgeon's attention need not be drawn to avoiding contact with an extended rigid retractor stem, and his freedom of movement about the operating table can be maximized. A second, and perhaps more important, advantage is that when a round-stemmed retractor is provided with a hinge, the folded stem section may function as a handle by which the retractor blade may be rotated away from the patient before its removal from the operating site.

A further improvement embodied in the present invention is an automatically locking retractor. Automatic locking is achieved by employing a retractor stem having a plurality of detent means disposed between the distal blade end and the proximal handle end and a retractor holder having a pivotal protuberance which is automatically displaceable when the retractor is drawn away from the incision, and which prevents the retractor from moving toward the incision by engaging selected detent means on the stem. This is easily accomplished in accordance with the present invention by spring loading the protuberance on the retractor holder.

The advantage to be obtained from this automatic locking capability is most significant. Conventional retractors may only be adjusted by loosening a nut or screw which secures the stem to the holder, moving the retractor to the desired degree of extension, and then refastening the nut or screw in order to secure the stem in its new position. By employing the automatic stem locking feature however, the surgeon need only engage the blade with the incision and then draw the stem out to the desired degree of retraction where it will be automatically secured by the spring-loaded protuberance of the holder without further attention. Further extension of the retractor may easily be achieved by simply drawing the stem further from the patient to the desired position, at which point it will again lock in place without any additional fastening operation being required. If a lesser degree of retraction is later desired, the protuberance on the holder may be manually pivoted away from the stem, releasing same so that while the protuberance remains in the manually pivoted position the blade is free to move towards the patient to the desired position, whereby upon releasing the protuberance, the latter will automatically engage the detent means of the stem and again lock the retractor into position.

Also encompassed by the present invention is an improved retractor holder having a body portion with means for attaching a retractor stem to the holder and a clip portion for attaching the holder to a retractor frame, in which the clip portion includes a receptacle for accommodating the retractor frame and a resilient member in opposed relation to the receptacle for removeably securing the retractor frame within the receptacle. Again, great savings of time and effort result from the use of the retractor holder of the invention, since such a clip-on holder can be attached or removed from the retractor frame at any time and at any position. The inconvenience of conventional slide-on holders, i.e., those which accommodate the retractor frame within the body of the holder, is therefore avoided, since any retractor holder attached to the retractor frame in other than its proper sequence can easily be moved without disturbing either other holders or the retractor frame support.

The clip-on holder of the present invention can be constructed in various configurations so as to be adapted for use on retractor frames of various cross-sectional shapes, such as round or flat frames. In addition, the improved holder may be advantageously constructed with the attaching means adjacent the resilient member such that a retractor held by the attaching means abuts the resilient member when the resilient member is in its undeformed position and prevents such deformation of the resilient member which would permit the release of the holder from the retractor frame.

A further aspect of the present invention is a retractor frame having a generally round cross-section and having an axially oriented groove. Such a retractor frame is suited for use with a retractor holder, also within the scope of the invention, having mounting means for accommodating a frame of round cross-section and further having a nub on the mounting means. When the holder is mounted on the frame the nub engages the complemental groove of the frame, rotation of the holder on the frame is prevented, and the retractor carried by the holder remains in a secure vertically-stable position.

Holders adapted for use with the grooved retractor frame of the invention may be of various configurations. For example, a solid-bodied holder having a cylindrical passage through which the frame is inserted may be provided with a raised ridge on the internal surface of the passage for engaging the grooved frame. Similarly, a clip-on holder may be provided with a protuberance, either on the interior surface of the receptacle or on the surface of the resilient member which contacts the retractor frame.

Additionally, the grooved frame of the present invention permits the use of both the holder of the invention and conventional holders, i.e., those without a protuberance for locking engagement of the groove.

A still further improvement encompassed by the present invention is a retractor holder which, in one embodiment, has a body portion and means for mounting the holder on a round cross-sectioned retractor frame, where the mounting means comprises a pair of spaced projections extending from the body portion, each of the projections having a concave edge portion for contacting the retractor frame, and a resilient member in opposed overlying relationship to the edge portions of the projections. In an alternative embodiment, the mounting means comprises a pair of spaced tabs extending from the body portion, each tab having a circular aperture through which the retractor frame may be passed. Either embodiment permits the holder to slide around curved portions of a round cross-sectioned retractor frame (such as a U-shaped frame), since the holder contacts the surface of the frame at only two points, rather than along the entire surface of the cylindrical passage of certain conventional holders. In addition, in either embodiment, each projection or tab may be provided with a protuberance for locking engagement with a grooved retractor frame, thereby further augmenting its advantages.

DESCRIPTION OF THE DRAWINGS

FIG. 2 is a perspective view of one of the improved retractor holders shown in FIG. 1.

FIG. 3 is a perspective view of the retractor holder of FIG. 2 to which is attached a retractor having a conventional flat stem and showing in phantom lines a tubular frame on which the holder is mounted.

FIG. 4 is a sectional view taken along line 4—4 of FIG. 2.

FIG. 5 is a perspective view of a second improved retractor holder of FIG. 1 and showing in phantom lines a grooved, tubular frame on which it is mounted.

FIG. 6 is a perspective view of a third improved retractor holder seen in FIG. 1.

FIG. 7 is an exploded perspective view of a fourth improved retractor holder seen in FIG. 1.

DETAILED DESCRIPTION

Figure 1:
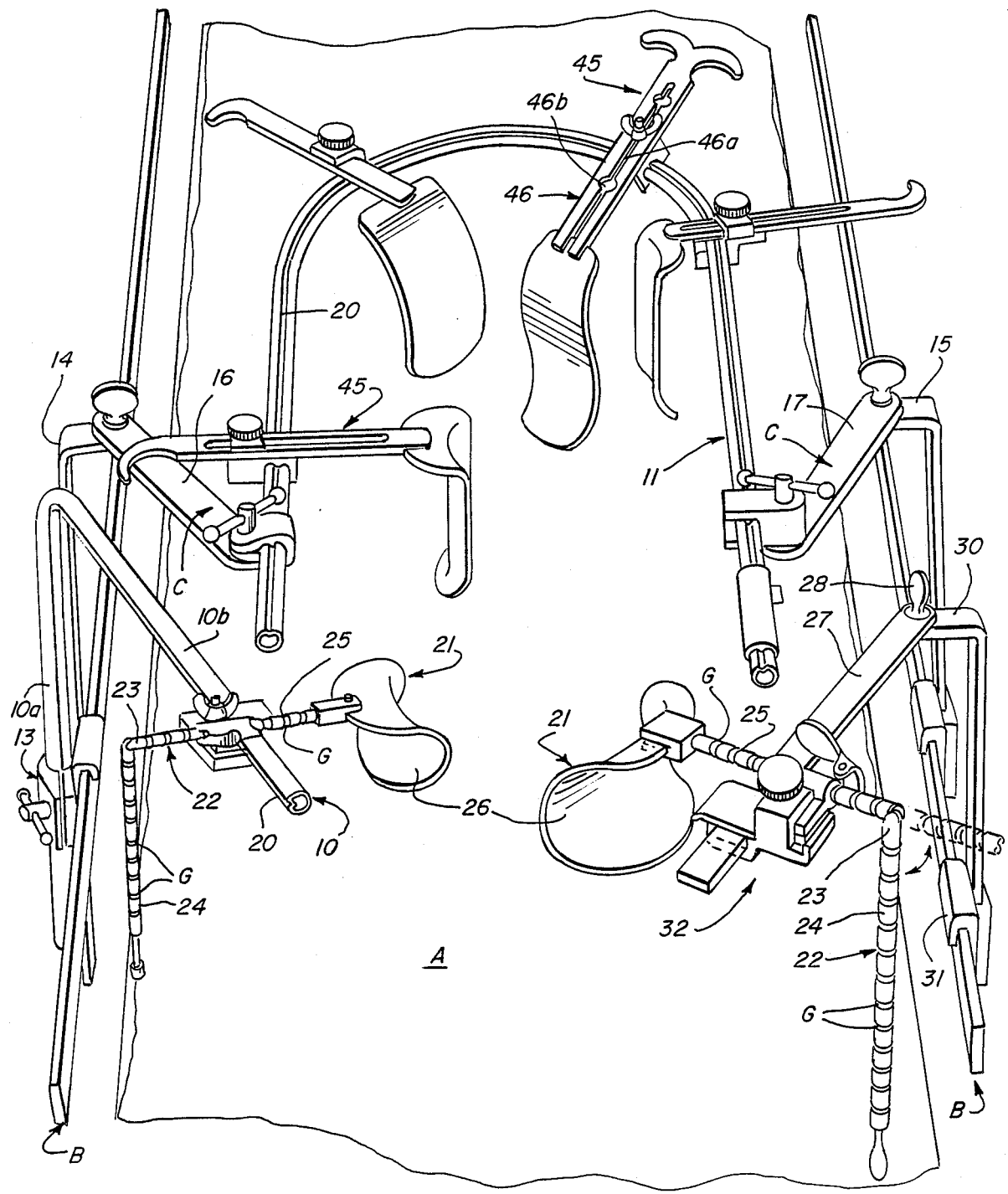
FIG. 1 is an elevated perspective fragmentary view of an operating table having attached to it a plurality of retractor frames, and, mounted on said frames, a variety of retractors affixed with a variety of retractor holders.

FIG. 1 illustrates an operating table A, having side rails B, to which frame supports C are attached. Various types of frames 10, 11 are utilized on which are mounted a predetermined number of retractors to be hereinafter described. As shown in FIG. 1 the frames 10, 11 are of tubular construction. Frame 10 is of an inverted L configuration and has the depending leg 10a thereof connected to one of the side rails B by a suitable clamp 13. The other leg 10b of the frame is in an elevated position with respect to the patient lying on the table A. Frame 11, on the other hand, has a U-shape and is disposed in an elevated, horizontal position above the table-supported patient. The frame 11 is maintained in the desired elevated position by a pair of upright supports 14, 15, one disposed on each side of the table A and secured to the table frame, not shown, by suitable clamps or the like, of conventional design. To the upper end of each support is adjustably connected an extension arm 16 or 17. The extension arm is normally formed of conventional flat bar stock. Once the arm has been properly positioned, it is retained in place by a turnbolt 18 which extends through an opening in the arm and is threaded into the end of the upright support. Both tubular frames 10, 11 are provided with at least one exterior, longitudinally extending indentation such as a groove 20. The groove is parallel to the axis of the tubular frame and the function of the groove will become apparent from the description to follow. Secured to the frames 10, 11 by various types of holders, to be hereinafter described, are various types of retractors.

One retractor 21, shown connected to the upper leg 10b of frame 10, includes an elongated stem 22 which is provided with a hinge 23 at approximately mid-length thereof. The hinge 23 forms the stem 22 into an outer section 24 and an inner section 25. Both sections are provided with a plurality of exposed circumferential grooves G of like configuration arranged in axially spaced relation. The hinge 23 serves a dual function: (1) it permits the outer section 24 to assume a right angle position with the inner section and thus, not interfere with the movements of the surgeon and his or her assistants; and (2) when in a right angle position, the outer section 24 provides a convenient handle to enable the retractor to be manually rotated about the axis of the inner section 25 thereby facilitating removal of the blade 26 from the inner end of section 25 without disturbing the patient. The shape and size of the blade 26 will depend upon the size and location of the incision and the physical dimensions of the patient.

As shown in FIG. 1, a second retractor of the same construction as retractor 21 is adjustably mounted on an extension arm 27, the latter being secured by a turnbolt 28 to the upper end of an upright support 30. Support 30 is similar to supports 14, 15 and is secured to a side rail B by a suitable clamp or attaching device 31. Attachment of the retractor 21 to the extension arm 27 is effected by a holder 32 which is shown more clearly in FIG. 7. The holder 32 as illustrated includes a bifurcated central body 33, a clip segment 34 extending laterally in one direction from a lower segment 33a of the body 33, a thumbscrew 35 mounted on an upper segment 33b of the body; and a stop segment 36 extending laterally from the body lower segment 33a and in a direction opposite from that of the clip segment 34. The clip segment includes a channel portion 37 which is sized to accommodate a portion of the extension arm 27 as will be described more fully hereinafter.

Overlying the body lower segment 33a, stop segment 36 and clip segment 34 is an elongated flat spring 38. The portion 38a of the spring adjacent the stop segment is attached thereto by suitable pins or rivets 40. The opposite end portion 38b of the spring is free and extends a short distance beyond clip segment 34. When attaching the holder 32 on the arm 27, the spring end portion 38b is brought into engagement with an edge of the extension arm and is distorted thereby, when manual pressure is applied, so as to allow the arm to slide between the spring end 38b and the clip segment 34 until it is aligned with the channel portion 37 whereupon a portion of the extension arm will be accommodated therein, see FIG. 1. The depth of the channel portion 37 is such that when the arm 27 is accommodated therein, the spring 38 will automatically return to its normal flat condition.

The thumbscrew 35 and flat spring 38 coact with the bifurcated central body 33 to secure an adapter piece 41 to the central body. The adapter piece facilitates connecting the round stem section 25 of the retractor 21 to the holder 32. As seen in FIG. 7, adapter piece 41 includes a flat base 42 which is sized so as to readily slide between the upper and lower segments 33b, 33a, respectively, of the body when thumbscrew 35 has been loosened a predetermined amount. Once the base 41 has been secured in place by the thumbscrew being drawn up tight against the base, the latter will overlie a substantial portion of the spring end portion 38b and press the latter into frictional engagement with the arm portion accommodated in the channel portion 37 and retain the holder in a fixed, selected position on the extension arm. An elongated depression 42a is provided in the upper surface of base 42 which is adapted to accommodate the concealed end of thumbscrew 35.

The base 42 has an exposed edge which is in the form of an elongated sleeve 43. The interior dimension of the sleeve permits the stem section 25 of the retractor 21 to readily slide endwise therein. Pivotally connected to the exterior of the sleeve and adjacent an end 43a of the sleeve furthest removed from the retractor blade 26, is a spring-loaded latch or lever 44. One end 44a of the latch is biased towards the sleeve axis so that it will automatically engage one of the external grooves G formed in the stem and restrain movement of the stem in a direction towards the patient's incision.

The opposite end 44b of the latch 44 is in an exposed, raised position and, when manually depressed will cause the latch to pivot about axis X thereby releasing the latch end 44a from the stem groove allowing the stem to be moved in either direction within the sleeve. The latch end 44b, when not depressed, will allow the stem the patients' incision and then be automatically locked in a desired position by the latch end 44a engaging a stem groove G. Notwithstanding that the stem is locked in a selected position, the retractor 21 can still be rotated about the stem section axis by reason of latch end 44a being disposed in a circumferential groove, thereby facilitating replacement of the blade 26 without having to disengage the entire retractor from the holder 32 or adjusting the position of the patient on the table A.

Locking a retractor 45 having a conventional flat elongated stem 46 on a tubular frame 11 is accomplished by a modified form of holder 47 as seen in FIGS. 2-4. The stem 46 normally is provided with an elongated longitudinally extending slot 46a.

Holder 47 is provided with a center body 48, a clip segment 50 extending laterally in one direction from a lower segment 48a of the center body. A stop segment 51 projects laterally from the opposite side of the lower segment 48a. It will be noted in FIG. 2 that the lower segment 48a and the clip segment 50 include parallel side walls V and W which are interconnected by a transverse base wall K. The portions of the side walls constituting the clip segment 50 are provided with semicircular cutouts 50a. The shape of the cutouts corresponds substantially to the curved exterior of the tubular frame 11.

A flat spring 52 is secured at one end 52a by pins or rivets 53 to the stop segment 51 and the opposite end 52b is free and overlies in spaced relation the base wall K of the clip segment 50. As seen in FIG. 2 the flat spring 52 is sized so as to fit between the side walls V and W. Spaced above the flat spring and extending in a cantilever relation from the side wall V of the center body is a flange 54 on which is mounted a thumbscrew 55. The space between flange 54 and flat spring 52 is adapted to accommodate the flat stem 46 of the retractor 45, see FIG. 3. Upon the thumbscrew 55 being drawn up tight against the stem 46, the latter will cause the free end 52b of the spring to be deflected downwardly thereby frictionally locking the holder 47 at selected position on the tubular frame 11. The thumbscrew 55 also locks the retractor stem in a fixed, selected position relative to the holder 47.

Rotation of holder 47 about tubular frame 11 is prevented by providing cutouts 50a of clip segment 50 with inwardly extending nubs 50b adapted to engage the external groove 20 formed in the tubular frame 11. Alternatively, the inward side of end 52b of spring 52 may be provided with an elongated protuberance adapted to engage the external groove of tubular frame 11 in order to prevent rotation of holder 47 about tubular frame 11.

Holder 47 is possessed of a feature wherein it may be readily snapped onto the tubular frame at any selected location without any adjustment of other holders previously mounted on the frame.

FIG. 5 depicts another embodiment of a holder 56 which includes a body section 57 having a pair of spaced, substantially parallel flange segments 57a, 57b which are interconnected at one end by a bail segment 58. Each flange segment is provided with a substantially round opening 60 through which a portion of the tubular frame 11 is adapted to slidably extend. A corresponding peripheral portion of each opening is provided with an inwardly extending nub 60a. The nubs are adapted to engage the external groove 20 formed in the tubular frame and thus, prevent rotation of the holder relative to the frame.

Disposed between the bail segment 58 and the flange openings 60 and affixed to the flange segments 57a, 57b is a transversely extending anchor piece 61. Affixed to the anchor piece at approximately the mid-length thereof is an upwardly extending stud bolt 62. The bolt terminates a substantial distance above the upper edges of the flange segments 57a, 57b, wee FIG. 5. The stud bolt is adapted to extend through the elongated slot 46a formed in the flat stem 46 of the retractor 45 shown in FIG. 3. The spacing between flange segments is slightly greater than the width of the flat stem 46 thus, enabling the flat stem to be disposed therebetween. It will be noted that the upper edge 58a of the bail segment 58 is recessed a slight amount from the upper edges of the flange segments The amount of the recess is approximately the same as the distance each opening 60 is from the upper edge of the respective flange segment.

The upper end 62a of the stud bolt is threadably engaged by a wing nut 63. When the nut 63 is drawn up tightly against the upper surface of the flat stem 46, the latter, in turn, will clamp the portion of the tubular frame 11 disposed within the openings 60 between the underside of the flat stem and the lower perimetric portions of the openings. Because of the serrated underside of the flat stem, as seen in FIG. 3 a positive nonslipping contact is made between the stem and the tubular frame. As seen in FIG. 1, the elongated slot 46a in the flat stem 46 of the retractor 45 is provided with one or more enlargements 46b which will allow the wing nut 63 and end 62a of the stud bolt to pass therethrough when the wings 63a of the wing nut are aligned with the slot.

Another embodiment of a holder 64 is shown in FIG. 6 for securing the retractor 21 to the upper leg 10b of the tubular frame support 10, see FIG. 1. Holder 64 is fabricated of a deformable material, preferably aluminum, and includes a body section 65 having a cylindrical passage 65a formed therein and disposed adjacent one side thereof. The passage 65a is provided with a longitudinally extending key or protuberance 66. The passage 65a is sized to slidably accommodate therein a portion of the tubular frame support 10. The protuberance 66 is adapted to slidably engage the external groove 20 formed in the support 10 and thus, prevent relative rotation between the holder 64 and the frame support. A cut or open end slot 67 is formed in the body section 65. The cut has three exposed open sides 67a and a concealed fourth side which terminates at the wall defining the passage 65a. Disposed transversely of the plane of cut 67 is a stud bolt 68. One end of the bolt is concealed within the body section 65 and is anchored to the portion 65b of the body section subtending the cut. The shank of the bolt spans the cut 67 and slidably extends through an opening formed in the portion 65c of the body section overlying the cut. The exposed end 68a of the bolt shank is threadably engaged by a wing nut 70. When the nut 70 is drawn up tightly against the exposed surface of body portion 65c the latter will be distorted downwardly towards body portion 65b with the result that the frame support portion accommodated in passage 65a will be fixedly held in place within the passage.

Formed in body portion 65c and offset with respect to the bolt shank is a second cylindrical passage 71. Passage 71 is disposed above passage 65a and is substantially perpendicular thereto. Passage 71 is sized so as to slidably accommodate the stem section 25 of the retractor 21. Pivotably connected to body portion 65c and adjacent the end of passage 71 furthest removed from the blade 26 of the retractor 21 is a spring biased latch 72. The construction and function of latch 72 are the same as aforedescribed with respect to the latch 44 of the adapter piece 44 of holder 32.

In holders 32 and 47, the thumbscrews thereof and in holders 56 and 64, the wing nuts thereof cannot be disassembled from the remainder of the holder; thus, eliminating the possibility of the thumbscrew or wing nut becoming lost or misplaced.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

I claim:

1. A surgical retractor adapted to be adjustably mounted on a supported holder, said retractor comprising an elongated stem having a cylindrical cross-section, having an exterior, and having blade means for contacting tissue adjacent an incision attached to one end of said stem; the exterior of said stem being provided with a plurality of axially spaced circumferential detent means adapted to be selectively engaged by a pivotal protuberance carried on the holder and being normally biased toward engagement with said detent means, thereby restraining longitudinal movement of the elongated stem in one direction.

2. The retractor of claim wherein the stem includes an inner section having an end thereof attached to said blade means, and an outer section hingedly connected to an opposite end of said inner section; said outer section, when in one position of hinged adjustment, providing a handle for exerting a manual pulling and rotational forces on said stem inner section and the blade means attached thereto.

3. A surgical retractor, a supported holder thereof, and a frame support having an exterior on which said holder is mounted in a selected position; said frame support having at least a portion thereof of a substantially cylindrical cross-sectional configuration with at least one longitudinally extending indentation formed in the exterior thereof, said frame support portion being substantially surrounded by a section of said holder, said holder section being provided with protruding means engaging the indentation of said frame support portion whereby the latter and the holder assume a non-rotating relation.

4. A surgical retractor, a supported holder therefor, and a frame support on which said holder is mounted in a selected position, said frame support having an exterior; said retractor having an elongated stem of a substantially cylindrical cross-sectional configuration and provided with a plurality of external longitudinally spaced circumferential detent means; said holder having a passage formed therein for slidably accommodating said retractor stem, and a pivotal protuberance mounted on said holder adjacent one end of said passage, said pivotal protuberance being adapted to automatically engage said detent means permitting relative sliding movement of said retractor stem in only one direction.

5. The surgical retractor, holder and frame support of claim 4, said pivotal protuberance being provided with manually engagable means for adjusting said pivotal protuberance to a release position whereby relative movement of said stem within said holder passage is unrestrained.

6. The surgical retractor, holder and frame support of claim 5 wherein the retractor stem includes hingedly connected inner and outer sections, at least said inner section being provided with said external circumferential grooves; the outer section being adapted to assume a handle-forming predetermined position of hinged adjustment relative to said inner section to facilitate manual pulling of said retractor in one direction and manual rotation of the retractor about the stem inner section as an axis.

7. The surgical retractor, holder and frame support of claim 6, wherein the retractor is adapted to be manually rotated about the stem inner section as an axis, when said latch is in engagement with a circumferential detent of said stem inner section.

8. The surgical retractor, holder and frame support of claim 4 wherein the holder includes a first member adjustably mounted on the frame support, and a second member removably connected to said first member, said second member having a portion thereof for slidably accommodating a retractor stem and means adjustably mounted on said portion and engaging said retractor stem for retaining same in a selected position of adjustment with respect thereto.

9. The surgical retractor, holder and frame support of claim 8 wherein the holder first member is provided with a bifurcated portion to which said second member is removably connected; said retractor stem and said frame support portion when connected to said holder being in angularly disposed relation.

10. A surgical retractor, a supported holder therefor, and a frame support on which said holder is mounted in a selected position, said frame support having an exterior; said frame support having at least a portion thereof of a substantially cylindrical cross-sectional configuration with at least one longitudinally extending indentation formed in the exterior thereof; said holder having a clip segment comprising a channel portion adapted to accommodate a portion of said frame support and spring means overlying said channel portion adapted for frictionally locking said holder at a selected position on said frame support, a portion of said clip segment engaging said frame support being provided with protruding means engaging the indentation of said frame support portion and coacting therewith whereby the latter and said holder assume a non-rotating relation.

11. A surgical retractor, a supported holder therefor, and a frame support on which said holder is mounted in a selected position, said frame support having an exterior; said retractor having an elongated stem of a substantially cylindrical cross-section configuration and provided with a plurality of external longitudinally spaced circumferential first means; said holder having a passage formed therein for slidably accommodating said retractor stem, and an adjustable complemental second means mounted on said holder adjacent one end of said passage, said second means being adapted to automatically engage said first means permitting relative sliding movement of said retractor stem in only one direction; and, said frame support has at least a portion thereof of tubular construction with the exterior thereof provided with at least one longitudinally extending indentation, and the holder is provided with a segment for substantially embracing the frame support portion, said holder segment being provided with protruding means for slidably engaging the indentation of said frame support portion.

* * * * *

UNITED STATES PATENT AND TRADEMARK OFFICE
CERTIFICATE OF CORRECTION

PATENT NO. : 4,813,401
DATED : March 21, 1989
INVENTOR(S) : Herman R. Grieshaber It is certified that error appears in the above-identified patent and that said Letters Patent is hereby corrected as shown below:

Column 6, line 66, after "stem" insert -- section 25 to only be manually pulled endwise away from --.
Column 8, line 5, after "57b," "wee" should be -- see --.
Column 8, line 13, after "segments" should be -- . --.

IN THE CLAIMS

Claim 2

Column 9, line 30, after "claim" insert -- 1, --.
Column 9, line 35, after "exerting", delete "a".

Claim 11

Column 10, line 51, "cross-section" should be -- cross-sectional --.

Signed and Sealed this

Fourteenth Day of November, 1989

Attest:

JEFFREY M. SAMUELS

*Attesting Officer*         *Acting Commissioner of Patents and Trademarks*